(12) United States Patent (10) Patent No.: US 8,821,016 B2
Yang et al. (45) Date of Patent: Sep. 2, 2014

(54) X-RAY IMAGING SYSTEM AND POSITIONING METHOD OF THE SAME

(75) Inventors: Soo Sang Yang, Suwon-si (KR); Jong Hwan Park, Osan-si (KR); Seung Hoon Shin, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 383 days.

(21) Appl. No.: 13/370,745

(22) Filed: Feb. 10, 2012

(65) Prior Publication Data

US 2012/0207274 A1 Aug. 16, 2012

(30) Foreign Application Priority Data

Feb. 15, 2011 (KR) ........................ 10-2011-0013383

(51) Int. Cl.
*A61B 6/08* (2006.01)
*A61B 6/00* (2006.01)
*G01N 23/04* (2006.01)

(52) U.S. Cl.
CPC ............... *A61B 6/547* (2013.01); *A61B 6/4464* (2013.01); *G01N 23/04* (2013.01)
USPC ........................................... 378/205; 378/62

(58) Field of Classification Search
CPC ........ A61B 6/4464; A61B 6/08; A61B 6/032; A61B 6/547; G01N 23/04
USPC ............ 378/62, 114–116, 193–198, 205, 207
See application file for complete search history.

(56) References Cited

U.S. PATENT DOCUMENTS

2011/0150179 A1* 6/2011 Kato ............................... 378/62

FOREIGN PATENT DOCUMENTS

JP 2001-504013 A 3/2001
JP 2005-204857 A 8/2005

OTHER PUBLICATIONS

Korean Office Action issued Apr. 23, 2013 in counterpart Korean Application No. 10-2011-0013383 (3 pages, in Korean).

* cited by examiner

*Primary Examiner* — Courtney Thomas
(74) *Attorney, Agent, or Firm* — NSIP Law (57) ABSTRACT

Disclosed are an X-ray imaging system and a positioning method of the same that automatically measure a relative positional relationship between devices. According to an aspect, an X-ray imaging system may include: a movable imaging device having a sensor; one or more beacons; a controller configured to analyze position information recognized by the sensor, to compare a relative position between the imaging device and the one or more beacons and to determine a position of the imaging device based on a positional error; and a drive device configured to move the imaging device to the position determined by the controller.

20 Claims, 7 Drawing Sheets

FIG. 7

X-RAY IMAGING SYSTEM AND POSITIONING METHOD OF THE SAME

CROSS-REFERENCE TO RELATED APPLICATION

This application claims the benefit of Korean Patent Application No. 2011-0013383, filed on Feb. 15, 2011, in the Korean Intellectual Property Office, the entire disclosure of which is incorporated herein by reference for all purposes.

BACKGROUND

1. Field

The following description relates to an X-ray imaging system and a positioning method of the same.

2. Description of the Related Art

An X-ray imaging system is an apparatus that acquires images of the inner parts of a body using X-rays. The X-ray imaging system may be used to examine interior parts of a body which are otherwise not viewable from the exterior. For instance, the X-ray imaging system may irradiate X-rays to the head or chest of the body and detect the X-rays transmitted through the head or chest of the body to acquire images of the inner parts of the body, so to help detect bodily injuries or diseases.

A typical X-ray imaging system generally includes an imaging device to generate and irradiate X-rays to a subject and an imaging table or imaging stand to receive the X-rays transmitted through the subject.

In recent years, X-ray imaging has largely become digitized, and, as a result, X-ray images are acquired using digital image acquisition technology rather than conventional film. For this reason, major portions of the X-ray imaging system have been automated. Examples of automation may include automatically matching the position of the imaging device with that of the imaging table or imaging stand ("auto-centering") and moving the imaging table or the imaging stand along the imaging device while maintaining a uniform positional relationship between the imaging device and the imaging table or the imaging stand upon movement of the imaging device ("auto-tracking").

It may be important to accurately set a relative positional relationship between the imaging device and the image table or the imaging stand at an initial stage to accurately perform the auto-centering or the auto-tracking, of the X-ray imaging system.

SUMMARY

According to one general aspect, a X-ray imaging system may include: a movable imaging device having a sensor, one or more beacons; a controller configured to analyze position information recognized by the sensor, to compare a relative position between the imaging device and the one or more beacons and to determine a position of the imaging device based on a positional error; and a drive device configured to move the imaging device to the position determined by the controller.

One or more of the beacons may include a signal emitting device. The emitting device may be configured to emit an infrared or ultrasonic signal. Alternatively or additionally, one or more of the beacons may include a predetermined pattern, or a display part configured to display a predetermined pattern.

The X-ray imaging system may further include an imaging table including the one or more beacons. The imaging table may include a movable imaging table. The imaging table may be configured to support a subject. The imaging table may include an X-ray receiving part configured to receive X-rays irradiated by the imaging device, and the one or more beacons may be provided at a surface of the X-ray receiving part.

The X-ray imaging system may further include a portable detector including the one or more beacons.

The X-ray imaging system may further include an imaging stand including the one or more beacons. The imaging stand may include: a main body; an X-ray receiving part movably coupled to the main body configured to receive X-rays irradiated by the imaging device, and the one or more beacons are provided at the X-ray receiving part.

The one or more beacons may emit or indicate identification information (ID) of a device.

According to another general aspect, a positioning method for an X-ray imaging system including: an imaging device having a sensor; an X-ray receiving device; one or more beacons recognized by the sensor; a controller configured to determine a position of the imaging device based on position information recognized by the sensor; and a drive device to move the imaging device, may be provided. The positioning method may include: acquiring information on positional relationships between the one or more beacons through the sensor; analyzing the information on positional relationships between the one or more beacons, comparing a relative position between the imaging device and the X-ray receiving device and determining a position of the imaging device based on a positional error through the controller; and moving the imaging device to the position determined by the controller through the drive device.

The positioning method may further include moving the imaging device into a zone where the sensor senses the one or more beacons.

Moreover, the positioning method may further include: calculating a positional error between a reference point of the X-ray receiving device and a reference point of the imaging device using the positional relationships between the one or more beacons acquired through the sensor at least two different positions.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Reference will now be made in detail to various embodiments, examples of which are illustrated in the accompanying drawings, wherein like reference numerals refer to like elements throughout.

Figure 1:
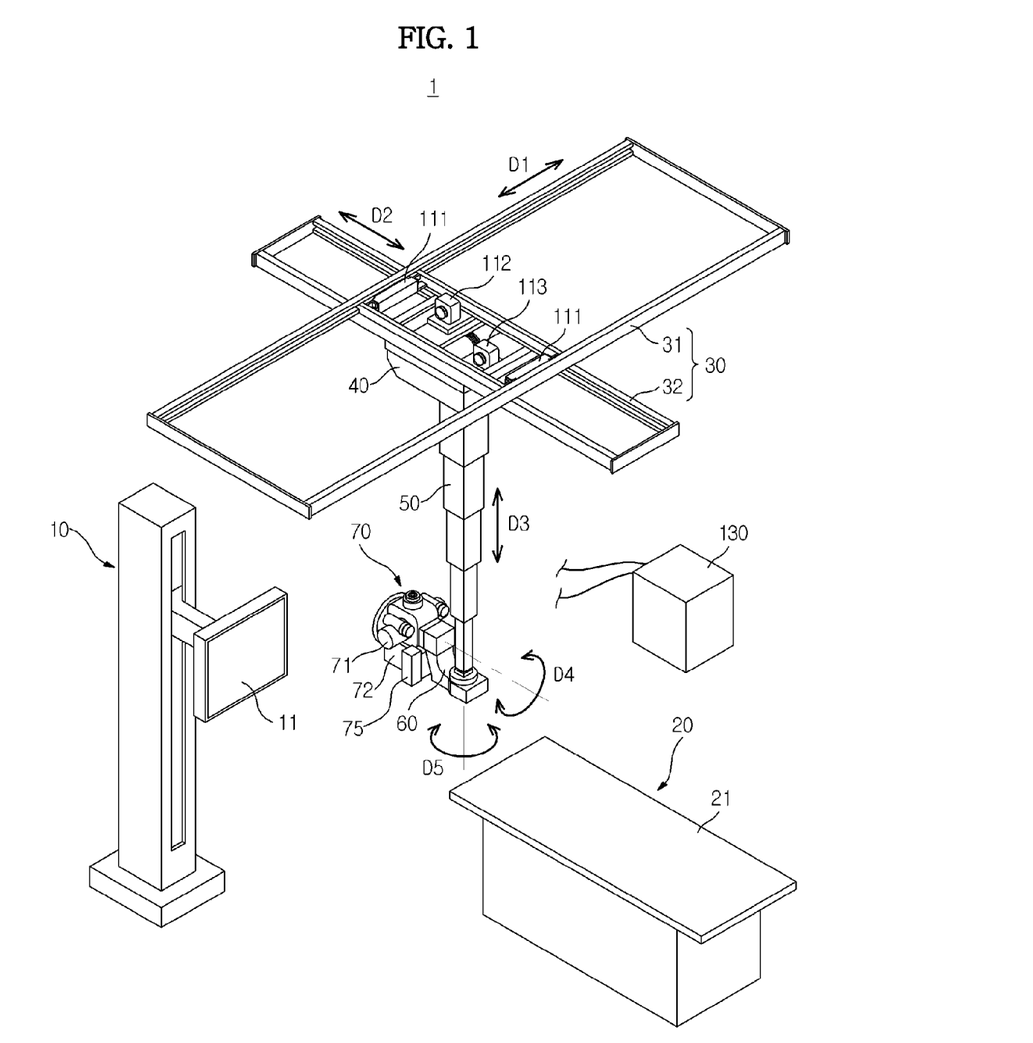
FIG. 1 is a perspective view showing an X-ray imaging system.
Figure 2:
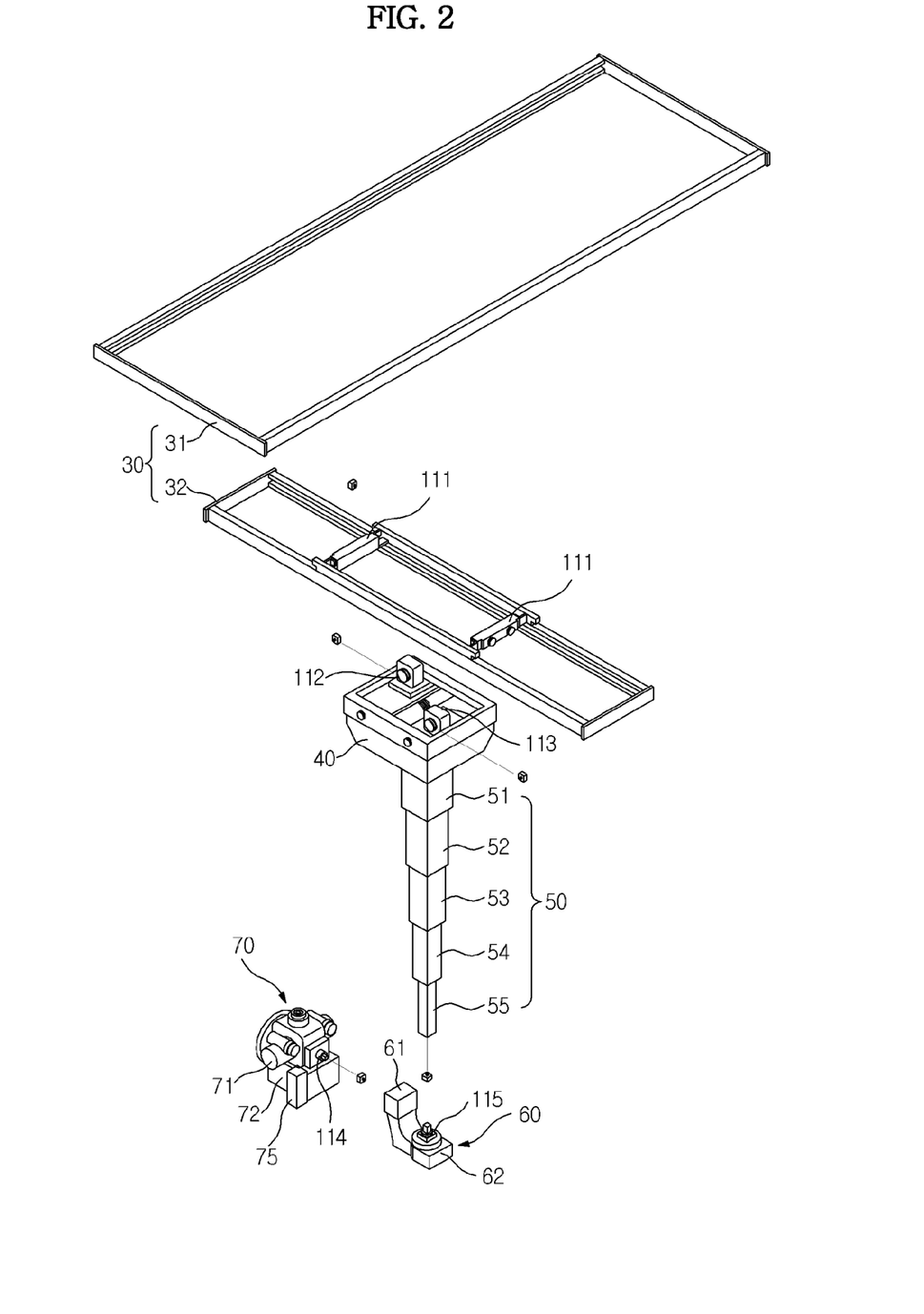
FIG. 2 is an exploded perspective view of the X-ray imaging system.

FIG. 1 is a perspective view showing an X-ray imaging system, and FIG. 2 is an exploded perspective view of the X-ray imaging system.

As shown in FIGS. 1 and 2, the X-ray imaging system 1 may generally include a guide rail 30, a moving carriage 40, a post frame 50, an imaging device 70 and drive devices 111, 112, 113, 114 and 115.

The guide rail 30, the moving carriage 40 and the post frame 50 are configured to move the imaging device 70 toward or away from a subject (e.g., patient). The subject may be a human patient in the case of medicine, or an animal patient in the case of veterinary medicine, for example. However, the subject could be an inanimate object in the case of non-medical use implementations, such as non-destructive testing of objects or the like.

The guide rail 30 includes a first guide rail 31 and a second guide rail 32 forming a predetermined angle with the first guide rail 31. The first guide rail 31 and the second guide rail 32 may extend perpendicularly to each other, for instance.

In some implementations, the first guide rail 31 may be mounted to the ceiling of a test room in which the X-ray imaging system 1 is installed. For example, the second guide rail 32 may be slidably mounted to the first guide rail 31 at the lower side of the first guide rail 31. A roller (or a bearing device) may be disposed at the first guide rail 30 and the second guide rail 32 may be connected to the roller (or the bearing device) so that the second guide rail 32 moves along the first guide rail 31.

The direction in which the first guide rail 31 extends may be defined as a first direction D1, and the direction in which the second guide rail 32 extends may be defined as a second direction D2. Consequently, the first direction D1 and the second direction C2 may be perpendicular to each other and parallel to the ceiling of the test room.

The moving carriage 40 is disposed at the lower side of the second guide rail 32 so that the moving carriage 40 is movable along the second guide rail 32. A roller (or a bearing device) may be disposed at the moving carriage 40 such that the moving carriage 40 is movable in the first direction D1 with the second guide rail 32 and in the second direction D2 along the second guide rail 32.

The post frame 50 may be fixed to the lower side of the moving carriage 40. In some embodiments, the post frame 50 may include a plurality of posts 51, 52, 53, 54 and 55.

The posts 51, 52, 53, 54 and 55 may be connected to one other to form a telescoping structure. Consequently, the length of the post frame 50 may be increased or decreased (e.g., in the vertical direction in a state in which the post frame 50 is fixed to the moving carriage 40). The direction in which the length of the post frame 50 increases or decreases may be defined as a third direction D3. Consequently, the third direction D3 may be perpendicular to the first direction D1 and the second direction D2.

The imaging device 70 is configured to emit or irradiate X-rays to the subject. The imaging device 70 may be an X-ray tube included in a general X-ray imaging system. The X-ray tube may include an X-ray generating source 71 that is configured to generate X-rays and a collimator 72 to guide the generated X-rays to the subject.

A rotary joint 60 is disposed between the imaging device 70 and the post frame 50. The rotary joint 60 couples or otherwise connects the imaging device 70 to the post frame 50 and supports load applied to the imaging device 70.

The rotary joint 60 may include a first rotary joint 61 connected to the lower end of the post frame 50 and a second rotary joint 62 connected to the imaging device 70.

The first rotary joint 61 is disposed so as to be rotatable about the central axis of the post frame 50 extending in the vertical direction of the test room. Consequently, the first rotary joint 61 may be rotated on a plane perpendicular to the third direction D3. At this time, the rotational direction of the first rotary joint 61 may be defined as a fourth direction D4 in which an axis parallel to the third direction D3 is rotated.

The second rotary joint 62 may be disposed so as to be rotatable on a plane perpendicular to the ceiling of the test room. Consequently, the second rotary joint 62 may be rotated in a direction in which an axis parallel to the first direction D1 or the second direction D2 is rotated. At this time, the rotational direction of the second rotary joint 62 may be defined as a fifth direction D5 in which an axis parallel to the first direction D1 or the second direction D2 is rotated.

The imaging device 70 may be connected to the rotary joint 60 so that the imaging device 70 is rotatable in the fourth direction D4 and the fifth direction D5. Also, the imaging device 70 may be connected to the post frame 50 via the rotary joint 60 so that the imaging device 70 is linearly movable in the first direction D1, the second direction D2 and the third direction D3.

The drive devices 111, 112, 113, 114 and 115 are provided to move the imaging device 70 in the first direction D1 to the fifth direction D5. The drive devices 110 may be electric motors, for example. Although it will be appreciated that other types of motors, such as pneumatic or hydraulic motors, might also be used.

The drive devices 111, 112, 113, 114 and 115 may be disposed at various positions in the system as desired. For example, the first drive device 111 may be disposed near the first guide rail 31 to move the second guide rail 32 in the first direction D1; the second drive device 112 may be disposed near the second guide rail 32 to move the moving carriage 40 in the second direction D2; and the third drive device 113 may be disposed in the moving carriage 40 to increase or decrease the length of the post frame 50 in the third direction D3. Also, the fourth drive device 114 may be disposed near the first rotary joint 61 to rotate the imaging device 70 in the fourth direction D4; and the fifth drive device 115 may be disposed near the second rotary joint 62 to rotate the imaging device 70 in the fifth direction D5.

In some implementations, the drive devices 110 may be connected to a power transmission unit, by which the drive devices 110 move or rotate the imaging device 70 in the first direction D1 to the fifth direction D5. For instance, the power transmission unit may include a belt and pulley, a chain and sprocket, a shaft, or the like to transfer and/or control driven power.

Figure 3:
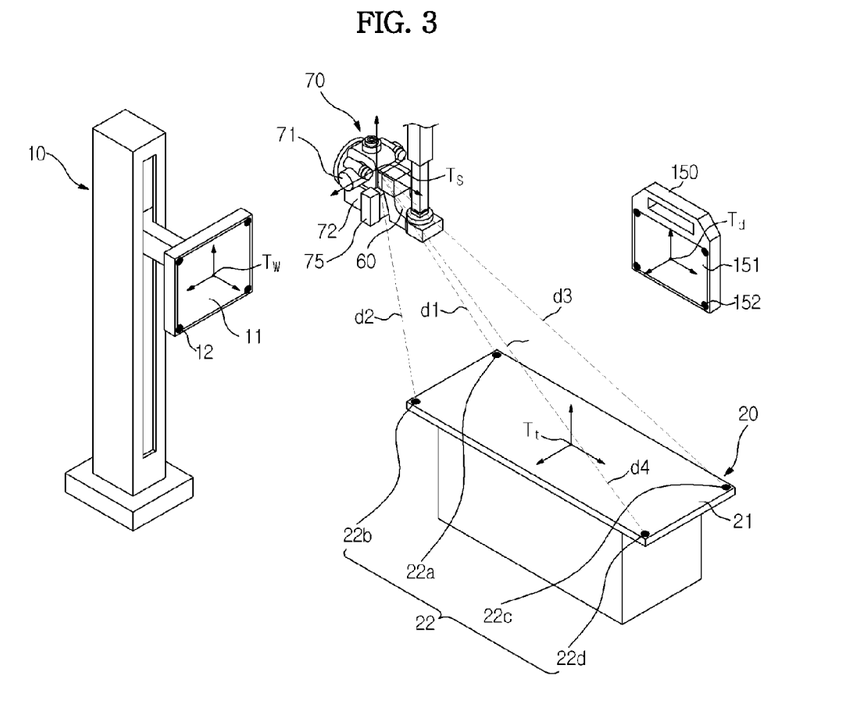
FIG. 3 is a perspective view showing the construction of a beacon sensor system used in the X-ray imaging system.

FIG. 3 is a perspective view showing the construction of a beacon sensor system used in the X-ray imaging system.

As shown in FIGS. 1 and 3, the X-ray imaging system 1 may further include an imaging stand 10, an imaging table 20 and a portable detector 150 having X-ray receiving parts 11, 21 and 151, respectively. The imaging table 20 may be movable (e.g., up or down, to the front or back, and/or side to side) in various embodiments. In some instances, the imaging stand 10, the imaging table 20 and the portable detector 150 may be referred to as an X-ray receiving device.

The X-ray receiving parts 11, 21 and 151 receive X-rays emitted from the imaging device 70 which may be transmitted through the subject. The received X-rays may be converted into electric signals using known digital technology, such as an image capturing device configured to image X-rays. For example, the electrical signals may be proportional to intensities of the received X-ray. As such, a diagnosis, using the results, may be made substantially in "real time."

At upper parts of the X-ray receiving parts 11, 21 and 151 are provided beacons 12, 22 and 152 which are used to determine or calibrate an initial positional error between the imaging device 70 and the X-ray receiving device.

The beacons 12, 22 and 152 may include one or more active devices that emit or send signals, and/or one or more passive devices that include predetermined pattern recognized by a sensor, such as marks. When the beacons are active devices, the beacons may be signal emitting devices, such as signal emitting devices configured to send infrared or ultrasonic signals. When the beacons are passive devices, the beacons may include a display part (e.g., a display device) that is configured to various patterns, as desired. Alternatively, the patterns or marks may be statically formed in a surface of the beacons by embossing, etching, painting or the like.

The beacons 12, 22 and 152 may further emit and/or convey identification information (ID) of a device, such as the X-ray receiving device. Based on the beacon ID, for instance, the kind and/or the size of the X-ray receiving device may be recognized using the beacons 12, 22 and 152, and a corresponding test or action may be carried out.

The imaging device 70 is provided with a sensor 75 configured to receive signals sent from the beacons 12, 22 and 152 and/or to recognize predetermined patterns of the beacons 12, 22 and 152.

In various implementations, the sensor 75 may be an infrared or ultrasonic sensor configured to receive the infrared or ultrasonic signals or an image sensor, such as a camera or a charged couple device (CCD). Other sensors might also be used which use other electromagnetic spectra.

A controller 130 may be provided that is configured to control one or more of the drive devices 111, 112, 113, 114 and 115 to move the imaging device 70 to a desired position. For example, if a user inputs a desired imaging position, the controller 130 determines the current position and the input imaging position and controls operations of the drive devices 110 to be driven. The imaging device 70 may be moved to the desired imaging position according to the operations of the drive devices 110. Also, the controller 130 may be configured to determine a positional error between a reference point Ts of the imaging device 70 and reference points Tt, Tw and Td of the X-ray receiving device based on position information of the X-ray receiving device recognized by the sensor 75.

A method of determining or calibrating a positional error between reference points of the imaging device 70 and the X-ray receiving device in an initial installation stage or in an initial driving stage will be described.

Figure 4:
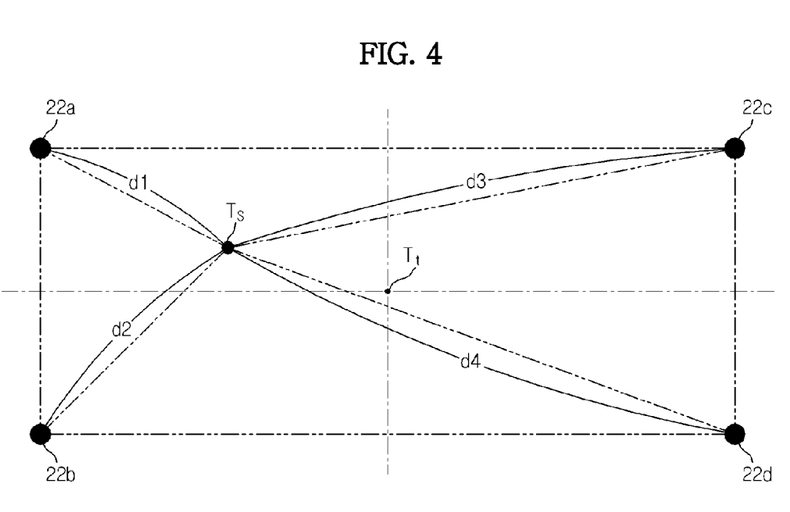
FIGS. 4 to 6 are views showing a principle of determining a positional error between reference points of an imaging device and an imaging table.
Figure 5:
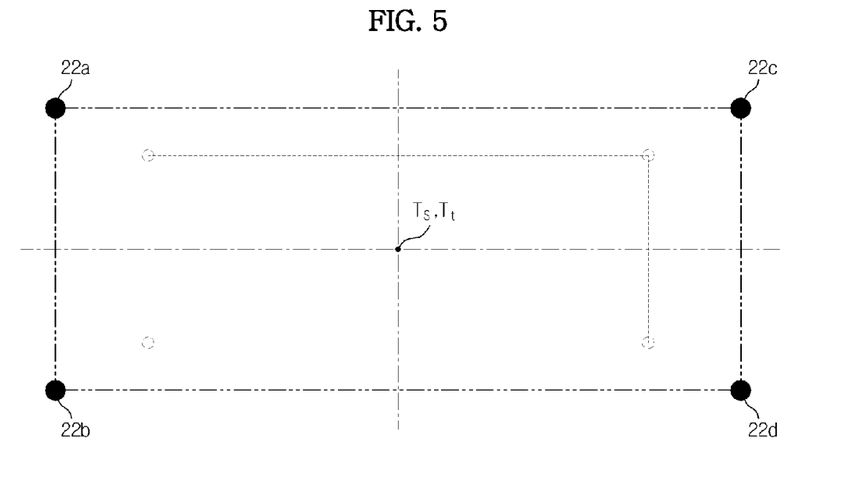
Figure 6:
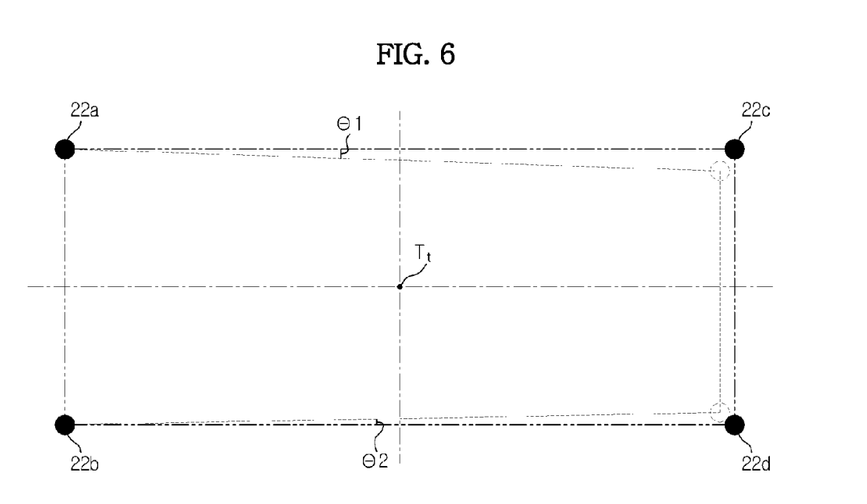
Figure 7:
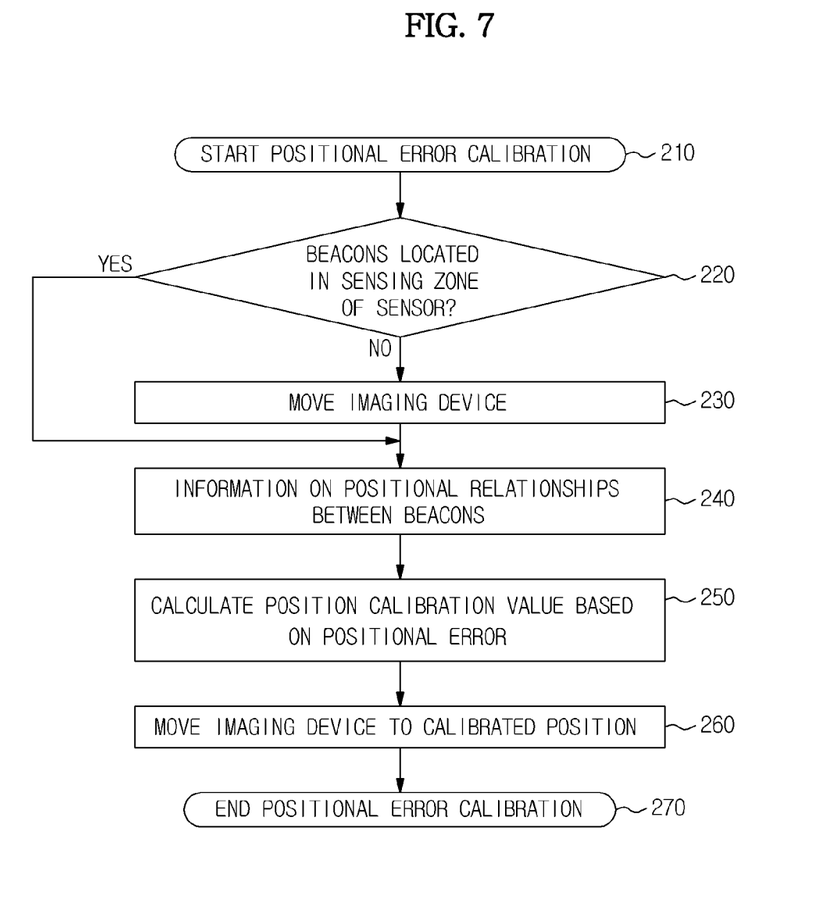
FIG. 7 is a flow chart showing a method of calibrating or determining a positional error between the reference points of the imaging device and the imaging table.

FIGS. 4 to 6 are views showing determining a positional error between reference points of the imaging device and the imaging table. FIG. 7 is a flow chart showing a method of calibrating or determining a positional error between the reference points of the imaging device and the imaging table.

While the following method is disclosed to be used for determining a positional error between the imaging device 70 and the imaging table 20, it will be appreciated that the same methodology may be used to calibrate or determine a positional error between the imaging device 70 and the imaging stand 10 or between the imaging device 70 and the portable detector 150 or between other devices.

In some embodiments, the reference point of the imaging table may be the center of the surface of the imaging table. However, it will be appreciated that other reference points may be used, such as one on the side or edges of the imaging table.

As shown in FIGS. 3 to 6, a method of determining a positional error between the reference point Ts of the imaging device 70 and the reference point Tt of the imaging table 20 may be based on distance measurements, angle measurements, or both.

When determining positioned errors based on distance measurements, distances d1, d2, d3 and d4 between the reference point Tt of the imaging table 20 and the beacons 22a, 22b, 22c and 22d may be calculated. When the sensor 75 of the imaging device 70 enters a zone where the sensor 75 can sense signals generated from beacons 22a, 22b, 22c and 22d or marks provided at the beacons 22a, 22b, 22c and 22d, the reference point Tt of the imaging table 20 can be calculated based on the calculated distances between the reference point Tt of the imaging table 20 and the beacons 22a, 22b, 22c and 22d. The calculated reference point Tt of the imaging table 20 may be compared with the reference point Ts of the imaging device 70 to determine or calculate a positional error generated at the initial installation stage or the initial driving stage of the X-ray imaging system 1 to obtain a distance which the reference point Ts of the imaging device 70 is to be moved based on the calculated error, i.e. a position calibration value.

Also, as shown in FIG. 5, when the imaging device 70 is moved vertically in a state in which the reference point Ts of the imaging device 70 and the reference point Tt of the imaging table 20 are disposed in parallel to each other in a direction perpendicular to the surface of the imaging table 20, the area of the zone formed by the beacons 22a, 22b, 22c and 22d provided at the imaging table 20, and a height relation between the reference point Ts of the imaging device 70 and the reference point Tt of the imaging table 20 can be obtained using a correlation between the vertical movement distance of the imaging device 70 and the area of the zone formed by the beacons 22a, 22b, 22c and 22d.

When determining positioned errors based on angle measurements, angle differences θ1 and θ2 may be sensed by the sensor 75 between (i) a zone 51 formed by the beacons 22a, 22b, 22c and 22d, at an original position, and (ii) a zone S2 formed by the beacons 22a, 22b, 22c and 22d, at a different position. The positional relationship between the reference point Ts of the imaging device 70 and the reference point Tt of the imaging table 20 and a position calibration value based on the positional relationship can be obtained using the angle differences θ1 and θ2 generated by the zones formed by the beacons 22a, 22b, 22c and 22d according to the movement distance or movement angle of the imaging device 70.

In determining the positional error between the reference point Ts of the imaging device 70 and the reference point Tt of the imaging table 20, a positional error calibrating process is started (in operation 210), and it is determined whether the sensor 75 is located within a zone where the sensor 75 can sense signals emitted from beacons 22a, 22b, 22c and 22d or marks/patterns provided at the beacons 22a, 22b, 22c and 22d (in operation 220).

If the sensor 75 is not located within the zone where the sensor 75 can sense signals generated from beacons 22a, 22b, 22c and 22d or the marks/patterns provided at the beacons 22a, 22b, 22c and 22d, the drive devices 110 are driven to move the imaging device 70 so that the sensor 75 is located within the zone where the sensor 75 can sense signals generated from beacons 22a, 22b, 22c and 22d or marks/patterns provided at the beacons 22a, 22b, 22c and 22d (in operation 230).

If the sensor 75 is located within the zone where the sensor 75 can sense signals generated from beacons 22a, 22b, 22c and 22d or the marks/patterns provided at the beacons 22a, 22b, 22c and 22d, information on positional relationships between the beacons 22a, 22b, 22c and 22d are obtained through the sensor 75 of the imaging device 70 (in operation 240).

The controller 130 analyzes the information on positional relationships between the beacons 22a, 22b, 22c and 22d to calculate the positional error between the reference point Ts of the imaging device 70 and the reference point Tt of the imaging table 20 and a position calibration value based on the positional error (in operation 250).

In addition, the controller 130 may be configured to automatically move the imaging device 70 to a calibrated position through the drive devices 110 (from operation 250) to calibrate the positional relationship between the reference point Ts of the imaging device 70 and the reference point Tt of the imaging table 20 (in operation 260), and the process of calibrating the positional error between the reference point Ts of the imaging device 70 and the reference point Tt of the imaging table 20 is completed (in operation 270).

The positional error generated at the initial installation stage or the initial driving stage of the X-ray imaging system 1 is automatically calculated using the sensor 75 and the beacons 22a, 22b, 22c and 22d to calibrate the positional relationship between the reference point Ts of the imaging device 70 and the reference point Tt of the imaging table 20, thereby improving convenience of use, reducing imaging time of the X-ray imaging system 1 and reducing operation costs.

Also, when the aforementioned sensor and one or more beacons are applied to a movable imaging table or a portable detector, the imaging device 70 may be automatically moved to a specific position of the movable imaging table or portable detector. As is apparent from the above description, a relative positional relationship between devices including the X-ray imaging system may be automatically measured to determine or calibrate a positional error between the devices, thereby improving convenience of use and reducing operation costs.

The methods described herein may be implemented using hardware components, software components, or a combination thereof, in some embodiments. For example, a controller may be implemented using one or more general-purpose or special purpose computers, such as, for example, a processor, an arithmetic logic unit, a digital signal processor, a microcomputer, a field programmable array, a programmable logic unit, a microprocessor or any other device capable of responding to and executing instructions in a defined manner. The controller may run an operating system (OS) and one or more software applications that run on the OS. The controller also may access, store, manipulate, process, and create data in response to execution of the software. For purpose of simplicity, the description of a controller is used as singular; however, one skilled in the art will appreciated that a controller may include multiple processing elements and multiple types of processing elements. For example, a controller may include multiple processors or a processor and a controller. In addition, different processing configurations are possible, such as parallel processors.

The software may include a computer program, a piece of code, an instruction, or some combination thereof, for independently or collectively instructing or configuring the controller to operate as desired. Software and data may be embodied permanently or temporarily in any type of machine, component, physical or virtual equipment, computer storage medium or device, or in a propagated signal wave capable of providing instructions or data to or being interpreted by the controller. The software also may be distributed over network coupled computer systems so that the software is stored and executed in a distributed fashion. In particular, the software and data may be stored by one or more computer readable recording mediums. The computer readable recording medium may include any data storage device that can store data which can be thereafter read by a computer system or a processing device. Examples of the computer readable recording medium include read-only memory (ROM), random-access memory (RAM), CD-ROMs, magnetic tapes, floppy disks, optical data storage devices. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein.

Although a few embodiments have been shown and described, it would be appreciated by those skilled in the art that changes may be made in these embodiments without departing from the principles and spirit thereof, the scope of which is defined in the claims and their equivalents.

What is claimed is:

1. An X-ray imaging system comprising:
   a movable imaging device having a sensor;
   one or more beacons;
   a controller configured to analyze position information recognized by the sensor, to compare a relative position between the imaging device and the one or more beacons and to determine a position of the imaging device based on a positional error; and
   a drive device configured to move the imaging device to the position determined by the controller.

2. The X-ray imaging system according to claim 1, wherein one or more of the beacons comprises a signal emitting device.

3. The X-ray imaging system according to claim 1, wherein one or more of the beacons comprises a predetermined pattern, or a display part configured to display a predetermined pattern.

4. The X-ray imaging system according to claim 1, further comprising: an imaging table including the one or more beacons.

5. The X-ray imaging system according to claim 4, wherein
   the imaging table includes an X-ray receiving part configured to receive X-rays irradiated by the imaging device, and
   the one or more beacons are provided at a surface of the X-ray receiving part.

6. The X-ray imaging system according to claim 1, further comprising a portable detector including the one or more beacons.

7. The X-ray imaging system according to claim 1, further comprising an imaging stand including the one or more beacons.

8. The X-ray imaging system according to claim 7, wherein the imaging stand comprises:
   a main body;
   an X-ray receiving part movably coupled to the main body configured to receive X-rays irradiated by the imaging device, and
   the one or more beacons are provided at the X-ray receiving part.

9. The X-ray imaging system according to claim 4, wherein the one or more beacons emit or indicate identification information (ID) of a device.

10. The X-ray imaging system according to claim 2, wherein the emitting device is configured to emit an infrared or ultrasonic signal.

11. The X-ray imaging system according to claim 4, wherein the imaging table comprises a movable imaging table.

12. The X-ray imaging system according to claim 4, wherein the imaging table is configured to support a subject.

13. A positioning method for an X-ray imaging system including: an imaging device having a sensor; an X-ray receiving device; one or more beacons recognized by the sensor; a controller configured to determine a position of the imaging device based on position information recognized by the sensor; and a drive device to move the imaging device, the method comprising:
   acquiring information on positional relationships between the one or more beacons through the sensor;
   analyzing the information on positional relationships between the one or more beacons, comparing a relative position between the imaging device and the X-ray receiving device and determining a position of the imaging device based on a positional error through the controller; and
   moving the imaging device to the position determined by the controller through the drive device.

14. The positioning method according to claim 13, further comprising: moving the imaging device into a zone where the sensor senses the one or more beacons.

15. The positioning method according to claim 14, further comprising: calculating a positional error between a reference point of the X-ray receiving device and a reference point of the imaging device using the positional relationships between the one or more beacons acquired through the sensor at least two different positions.

16. The positioning method according to claim 15, wherein
   the X-ray receiving device comprises an imaging table having an X-ray receiving part configured to receive X-rays irradiated by the imaging device, and
   the one or more beacons are provided at the X-ray receiving part.

17. The positioning method according to claim 16, wherein the imaging table comprises a movable imaging table.

18. The positioning method according to claim 15, wherein the X-ray receiving device comprises a portable detector including the one or more beacons.

19. The positioning method according to claim 15, wherein
   the X-ray receiving device comprises an imaging stand having an X-ray receiving part configured to receive X-rays irradiated by the imaging device, and
   the one or more beacons are provided at the X-ray receiving part.

20. The positioning method according to claim 15, wherein the one or more beacons emit an infrared or ultrasonic signal.

* * * * *